United States Patent [19]

Esteve Soler

[11] 4,342,763

[45] Aug. 3, 1982

[54] P-CHLOROACETOPHENONE OXIME COMPOUNDS AND PHARMACEUTICAL COMPOSITIONS

[75] Inventor: Jose Esteve Soler, Barcelona, Spain

[73] Assignee: Provesan S.A., Geneva, Switzerland

[21] Appl. No.: 119,104

[22] Filed: Feb. 6, 1980

[30] Foreign Application Priority Data

Feb. 13, 1979 [FR] France ............................ 79 03617

[51] Int. Cl.³ ................ C07D 295/12; A61K 31/445; A61K 31/535
[52] U.S. Cl. ............................ 424/248.56; 424/267; 424/274; 424/327; 544/162; 546/232; 260/326.5 L; 564/256
[58] Field of Search ...................... 564/256; 544/162; 546/232; 260/326.5 L; 424/248.56, 267, 274, 327

[56] References Cited

U.S. PATENT DOCUMENTS 3,692,835  9/1972  Van Dijk et al. ................ 564/256

OTHER PUBLICATIONS

Rossi et al., Chem. Abstracts, vol. 61 (1964), No. 10545 and 10546.

Kurihara et al., Chem. Abstracts, vol. 87 (1977), No. 134,481n.

Primary Examiner—Robert W. Ramsuer
Attorney, Agent, or Firm—Dressler, Goldsmith, Shore, Sutker & Milnamow, Ltd.

[57] ABSTRACT

Derivatives of p-chloroacetophenone oxime, the preparation thereof and the use thereof as medicaments.

The compounds of the invention correspond to the general formula I

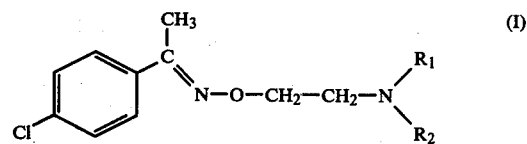

wherein $R_1$ and $R_2$ each represent a lower alkyl radical, preferably a $C_1$ to $C_4$ radical, or, in association with the nitrogen atom to which they are linked, form a saturated heterocyclic group, and the physiologically acceptable acid addition salts.

The compounds of the invention are useful as medicaments and particularly as analgesics, antipyretics, anti-inflammatory agents and antitussives.

10 Claims, No Drawings

P-CHLOROACETOPHENONE OXIME COMPOUNDS AND PHARMACEUTICAL COMPOSITIONS

The present invention concerns novel derivatives of p-chloroacetophenone oxime, the preparation thereof and the use thereof as medicaments.

The novel derivatives according to the present invention correspond to following general formula I:

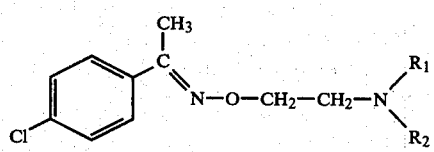

wherein $R_1$ and $R_2$ each represent a lower alkyl radical, preferably a $C_1$ to $C_4$ radical, or, in association with the nitrogen atom to which they are linked, form a saturated heterocyclic group.

The present invention also relates to the acid addition salts of physiologically acceptable acids such as hydrohalides and especially hydrochlorides, of the derivatives of formula I.

The derivatives of general formula I and their acid addition salts enjoy valuable pharmacological, analgesic, antipyretic, anti-inflammatory and anti-tussive properties. The present invention therefore also concerns the use of such compounds as medicaments, and the pharmaceutical compositions containing such compounds as their active principle.

The preferred derivatives of the invention are those of general formula I, wherein $R_1$ and $R_2$ are identical and represent a methyl or ethyl radical, preferably an ethyl radical, or wherein $R_1$ and $R_2$, in association with the nitrogen atom to which they are linked, form a pyrrolidino, piperidino or morpholino group.

The present invention also concerns the preparation of the derivatives of general formula I. In accordance with the process of the invention, the oxime of p-chloroacetophenone of the following formula II:

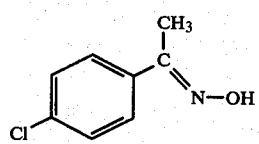

is reacted with a substituted halo-ethylamine of general formula III

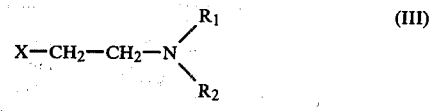

wherein:
X represents a halogen atom, especially chlorine; and
$R_1$ and $R_2$ each represent a lower alkyl radical, preferably a $C_1$ to $C_4$ radical, or, in association with the nitrogen atom to which they are linked, form a saturated heterocyclic group.

Preparation of p-chloroacetophenone-O-(2-dimethyl aminoethyl)oxime in the form of a free base and in the form of a hydrohalide, will now be described hereinafter in greater detail by way of non-limiting example.

EXAMPLE 1 p-Chloroacetophenone-O-(2-dimethylaminoethyl)oxime 17.0 g (0.1 mole) of p-chloroacetophenone oxime, 2.5 g (0.1 mole) of sodium hydride and 200 ml of anhydrous dioxan are added in a 500 ml Erlenmeyer flask provided with a stirring means, a cooler and a calcium chloride tube.

The temperature is maintained at 70° C. for 3 hours and then 11.8 g (0.11 mole) of dimethylchloroethylamine is added.

The temperature is maintained at 70° C. for 12 hours, then the flask is allowed to cool and the content is poured into 2 liters of water. Extraction with ethylether gives p-chloroacetophenone-O-(2-dimethylaminoethyl)oxime in the form of an oil, with a boiling point of 148°–150° C. at 0.1 mm Hg.

In order to produce the corresponding hydrohalide, for example hydrochloride, the free base is reacted with ethanol saturated with hydrohalide acid, for example hydrochloric acid, followed by evaporation under vacuum. Recrystallisation is then effected, for example from isopropanol.

The resulting hydrochloride has a melting point of from 172° C. to 174° C.

EXAMPLES 2 TO 5

By operating in the same manner as that described in Example 1, diethyl, pyrrolidino, piperidino and morpholino derivatives are obtained, by using the suitably substituted chloroethylamine.

Table I given hereinafter sets out a certain number of physical-chemical constants relating to the above-indicated derivatives, in particular the crystallisation solvents, melting points and characteristic peaks on the NMR spectra.

TABLE I

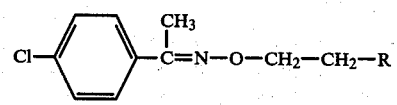

| Example No. | R | Free base boiling point | Hydrochloride crystallisation solvent | Hydrochloride melting point | Hydrochloride yield | NMR* |
|---|---|---|---|---|---|---|
| 1 | −N(CH$_3$)(CH$_3$) | 148° C. 0.1 mm Hg | isopropanol | 172–4° C. | 62% | 7.3 (4H,q); 4.2 (2H,t); 2.55 (2H,t); 2.17 (6H,s); 2.08 (3H,s) |

TABLE I-continued

| No | R (amine) | b.p. | solvent | m.p. | yield | NMR* |
|---|---|---|---|---|---|---|
| 2 | −N(CH₂—CH₃)(CH₂—CH₃) | 153° C. 0.5 mm Hg | iso-propanol/ether | 133–4° C. | 67% | 7.3 (4H,q); 4.2 (2H,t); 2.65 (2H,t); 2.40 (4H,t); 2.08 (3H,s); 1.0 (6H,t) |
| 3 | −N (pyrrolidine) | 183° C. 1 mm Hg | acetonitrile | 171–3° C. | 68% | 7.3 (4H,q); 4.2 (2H,t); 2.65 (2H,t); 2.5 (4H,m); 2.07 (3H,t); 1.7 (4H,m) |
| 4 | −N (piperidine) | 178° C. 0.5 mm Hg | iso-propanol/ether | 173–5° C. | 71% | 7.3 (4H,q); 4.2 (2H,t); 2.53 (2H,t); 2.35 (4H,m); 2.08 (3H,s); 1.38 (6H,m) |
| 5 | −N O (morpholine) | 170° C. 0.2 mm Hg | Et—OH | 197–9° C. | 45% | 7.3 (4H,q); 4.2 (2H,t); 2.5 (10H,m); 2.1 (3H,t) |

*solvent, CCl₄, internal reference, TMS, displacement in δ
m = multiplet, s = singlet, t = triplet, q = quadruplet

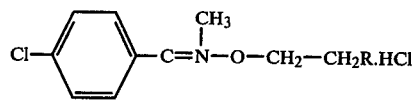

$$Cl-C_6H_4-C(CH_3)=N-O-CH_2-CH_2R \cdot HCl$$

| Example No. | R | | Analysis % (hydrochloride) | | | |
|---|---|---|---|---|---|---|
| | | | C | H | N | Cl |
| 1 | −N(CH₃)(CH₃) | Calculated | 52.00 | 6.54 | 10.10 | 25.56 |
| | | actual | 51.92 | 6.60 | 9.93 | 25.71 |
| 2 | −N(CH₂—CH₃)(CH₂—CH₃) | calculated | 55.08 | 7.27 | 9.17 | 23.23 |
| | | actual | 55.21 | 7.19 | 9.19 | 23.39 |
| 3 | −N (pyrrolidine) | calculated | 55.47 | 6.65 | 9.24 | 23.37 |
| | | actual | 55.30 | 6.78 | 9.32 | 23.49 |
| 4 | −N (piperidine) | calculated | 56.80 | 6.98 | 8.83 | 22.35 |
| | | actual | 56.78 | 7.00 | 8.91 | 22.51 |
| 5 | −N O (morpholine) | calculated | 52.65 | 6.32 | 8.77 | 22.22 |
| | | actual | 52.49 | 6.49 | 8.70 | 22.41 |

Analgesic activity

The analgesic activity of the derivatives of general formula I was determined on male mice weighing between 20 and 25 g. The substance to be tested is administered in the form of a 5% suspension in gum arabic orally by means of an oesophageal sound or probang. The volume of the solution administered is 25 ml/kg and the concentration of the substance being tested is changed according to the dose ministered.

Pain is caused to the animals by means of an intraperitoneal injection of 0.2 ml/20 g of acetylcholine bromide solution, in a concentration of 0.32 mg/ml. 5 minutes before administration of the substance being tested, acetylcholine is injected in a batch of 5 mice. The substance to be tested is then administered, and the acetylcholine injection is repeated after 20, 40, 80, 120 and 160 minutes. A count is always taken of the number of contortions per injection of acetylcholine over a period of 5 minutes.

Analgesic activity is calculated by means of the following formula:

$$It = 100 - (Nt/No) \cdot 100 = 100 \, l(-Nt/No)$$

wherein

It = inhibition of pain after 5 minutes:

No = number of contortions before administration of the substance

Nt = number of contortions after t minutes of administration of the substance.

Several doses of each product are administered, in order to be able to determine the 50 percent analgesic dose (DA-50).

With each of the doses, It is calculated at 20, 40, 80, 120 and 160 minutes. The average of these five values of It for each dose is taken as the analgesic action. The analgesic actions are shown diagrammatically, in dependence on the logarithm of the corresponding dose.

This curve is used to obtain the 50 percent analgesic dose, that is to say, the dose which produces a 50 percent analgesic action.

By way of example, Table II hereinafter sets forth the results obtained with the derivatives of Examples 1 to 5.

Acute Toxicity

Acute toxicity is determined by i.p. administration to mice weighing from 20 to 25 g, using batches of 6 animals. Several doses are administered, in a geometric progression. The observation period is 72 hours. The 50 percent lethal dose (DL-50) is calculated graphically by means of logarithmic-probabilistic paper.

By way of example, Table II hereinafter sets out the results obtained with the derivatives of Examples 1 to 5.

TABLE II

| Example No. | Derivative | Doses in mg/kg | |
| --- | --- | --- | --- |
| | | DA-50 | DL-50 |
| 1 | p-chloroacetophenone-O-(2-dimethylaminoethyl) oxime hydrochloride | 75 | 98 |
| 2 | p-chloroacetophenone-O-(2-diethylaminoethyl) oxime hydrochloride | 15 | 107 |
| 3 | p-chloroacetophenone-O-(2-pyrrolidinoethyl) oxime hydrochloride | 20 | 214 |
| 4 | p-chloroacetophenone-O-(2-piperidinoethyl) oxime hydrochloride | 57 | 112 |
| 5 | p-chloroacetophenone-O-(2-morpholinoethyl) oxime hydrochloride | 67 | 638 |

Anti-inflammatory activity

Anti-inflammatory activity is determined on male rats of Sprague-Dawley stock. An oedema is caused in the paw by subplantar injection of a 1% carrageenin solution. The volume of the paw before oral administration of the product, after 3 hours and after 5 hours, is measured with a plethysmograph. Anti-inflammatory activity is calculated, relative to a reference batch. By way of example, Table III hereinafter sets forth the results obtained with the derivatives of Examples 1 to 5.

TABLE III

| Example No | Derivative | Dose (mg/kg) | Anti-inflammatory activity | |
| --- | --- | --- | --- | --- |
| | | | 3 hours | 5 hours |
| 1 | p-chloroacetophenone-O-(2-dimethylamino-ethyl) oxime hydrochlorate | 27 | 29 | 41 |
| 2 | p-chloroacetophenone-O-(2-diethylamino-ethyl) oximine hydrochlorate | 305 | 53 | 49 |
| 3 | p-chloroacetophenone-O-(2-pyrrolidino-ethyl) oximine hydrochlorate | 303 | 47 | 53 |
| 4 | p-chloroacetophenone-O-(2-piperidino-ethyl) oximine hydrochlorate | 317 | 48 | 47 |
| 5 | p-chloroacetophenone-O-(2-morpholino-ethyl) oximine hydrachlorate | 319 | 25 | 40 |

Anti-tussive activity in guinea-pigs

Guinea-pigs of both sexes, weighing from 350 to 400 g, are used. This procedure uses a modification of the methods described by Ellis [J. Med. Chem. 6, 115 (1963)] in rats and by Charlier [Arch. Int. Pharmacodyn, 134, 306 (1961)] in guinea-pigs.

Each animal is placed in a glass flask which is 2 liters in capacity, for a period of 3.5 minutes. In the first minute, an air flow of 0.65 ml/minute is passed. During the next 30 seconds, air containing ammonia is passed through the flask, this being achieved by causing it to bubble through a solution of 24° Be ammonia 50% diluted with distilled water. The ammonia is then stopped, and air is again circulated at the same flow rate (0.65 ml/min) for a further 2 minutes.

The glass flask is connected to a Hewlett Packard 270 transducer so as to be able to record the respiratory movements of the animal by means of a Hewlitt Packard 7702-B polygraph for the last two minutes for which the animal remains in the flask. The animals respond to the stimulation produced by the flow of ammonia-bearing air by fits of coughing which can be measured on the graph by virtue of producing a movement of greater amplitude than the normal respiratory movements of the animals. Once the first reading has been taken, the vehicle used (control), the standard product or the product to be tested are administered to each animal, in a sequence established by means of a random number table. The compounds were administered subcutaneously in a proportion of 2 ml/kg of solution (or suspension) whose concentration varies in dependence on the dose administered. 60 minutes after administration of the products, each animal was replaced in the glass flask and subjected to the above-described procedure, under identical conditions.

Counts made in respect of the coughing fits for each animal, before and after administration of the different compounds, make it possible to calculate the reduction in the percentage of responses. Anti-tussive activity is calculated by deducting the percentage reduction in responses of the control from the reduction achieved with the product being tested. By way of example, Table IV hereinafter sets forth the results obtained with the derivative of Example 5.

TABLE IV

| Derivative | Dose | Number of animals | Average R.P.R. ± E | Anti-tussive activity |
| --- | --- | --- | --- | --- |
| 5% gum arabic | 2 ml/kg | 33 | 17.3 ± 4.4 | 0.0 |
| Codein | 18 mg/kg | 23 | 37.4 ± 6.5 | 20.1 |
| Dextrometorphane | 38 mg/kg | 8 | 41.6 ± 10.1 | 24.3 |
| p-chloroacetophenone-O-(2-morpholinoethyl) | 32 mg/kg | 8 | 57.8 ± 6.7 | 40.2 |

TABLE IV-continued

| Derivative | Dose | Number of animals | Average R.P.R. ± E | Anti-tussive activity |
|---|---|---|---|---|
| oxime hydrochloride | | | | |

E: type difference from average
R.P.R.: response percentage reduction, corresponding to:
$$100 \times \frac{\text{No. of coughing fits of the reference} - \text{No. of coughing fits of the animal under test}}{\text{No. of coughing fits of the reference}}$$

Bearing in mind their good pharmacodynamic properties, the derivatives of general formula I are therefore suitable for use in human and/or veterinary medicine, as analgesic, anti-pyretic, anti-inflammatory and anti-tussive agents.

The pharmaceutical compositions which, in accordance with the invention, contain, in addition to a pharmaceutically acceptable carrier, at least one derivative of general formula I, enjoy a very wide field of therapeutic use and can be employed in particular in traumatology, surgery, rheumatology, odontostomatology, otorhinolaryngology, pneumology, cardiology, gynecology and urology. Such pharmaceutical compositions will be for example used for treating various painful manifestations, headaches, migraines, toothache, neuralgias, menstrual pains, inflammatory rheumatisms, arthrosic pains, febril conditions, colds, influenzas and seasonal infections.

In human therapy, the proposed dose in respect of the derivatives of the present invention is between about 100 and 500 mg/day, being administered for example in the form of compressed tablets, jelly-type pills, suppositories or injectable solutions.

Four particular gallenic forms of the derivatives according to the present invention will be set forth hereinafter by way of example.

| Example of a formula for compressed tablets | |
|---|---|
| p-chloroacetophenone-O-(2-pyrrolidino-ethyl) oxime hydrochloride | 250 mg |
| Starch | 125 mg |
| Primogel | 25 mg |
| Lactose | 132.5 mg |
| Polyvinylpyrrolidione | 25 mg |
| Magnesium stearate | 5 mg |
| compressed tablet weight | 562.5 mg |
| Example of a formula for jelly-type pill | |
| p-chloroacetophenone-O-(2-pyrrolidino-ethyl) oximine hydrochloride | 250 mg |

| -continued | |
|---|---|
| Avicel ph 102 | 190 mg |
| Aerosil-200 | 3.75 mg |
| Magnesium stearate | 6.25 mg |
| jelly pill weight | 450 mg |
| Example of a formula for suppository | |
| p-chloroacetophenone-O-(2-pyrrolidino-ethyl) oxime hydrochloride | 0.3 g |
| Monolein | 2.5 g |
| suppository weight | 2.8 g |
| Example of a formula for an injectable solution ampoule | |
| p-chloroacetophenone-O-(2-pyrrolidino-ethyl) oxime hydrochloride | 200 mg |
| Water to be injectable, q.s. | 2 ml |

What is claimed is:
1. A compound of general formula I

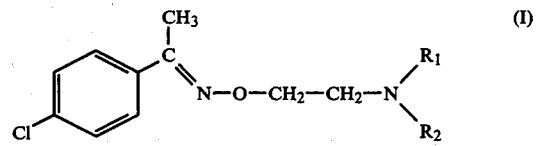

wherein $R_1$ and $R_2$ in association with the nitrogen atom to which they are linked, form a pyrrolidino, piperidino or morpholino group, and the physiologically acceptable acid addition salts.

2. A hydrohalide salt of a compound according to claim 1.

3. A hydrochloride salt of a compound according to claim 1.

4. p-Chloroacetophenone-O-(2-pyrrolidinoethyl)oxime.

5. p-Chloroacetophenone-O-(2-pyrrolidinoethyl)oxime hydrochloride.

6. p-Chloroacetophenone-O-(2-piperidinoethyl)oxime.

7. p-Chloroacetophenone-O-(2-piperidinoethyl)oxime hydrochloride.

8. p-Chloroacetophenone-O-(2-morpholinoethyl)oxime.

9. p-Chloroacetophenone-O-(2-morpholinoethyl)oxime hydrochloride.

10. An analgesic, anti-inflammatory and anti-tussive pharmaceutical composition comprising a pharmaceutically acceptable carrier, and an effective amount of at least one compound of general formula I according to claim 1.

* * * * *